United States Patent [19]

Dittmann

[11] Patent Number: 5,176,635
[45] Date of Patent: Jan. 5, 1993

[54] TWIN-CHAMBER SYRINGE FILLED WITH A CHARGE OF ACTIVITY-SENSITIVE HUMAN PROTEIN AS ACTIVE SUBSTANCE

[75] Inventor: Otto Dittmann, Brensbach-Wallbach, Fed. Rep. of Germany

[73] Assignee: Alpha-Therapeutic GmbH, Langen, Fed. Rep. of Germany

[21] Appl. No.: 455,344

[22] PCT Filed: Mar. 1, 1989

[86] PCT No.: PCT/EP89/00202

§ 371 Date: Dec. 6, 1989

§ 102(e) Date: Dec. 6, 1989

[87] PCT Pub. No.: WO89/07934

PCT Pub. Date: Sep. 8, 1989

[30] Foreign Application Priority Data

Mar. 1, 1988 [DE] Fed. Rep. of Germany ....... 3806562

[51] Int. Cl.⁵ .............................................. A61K 9/00
[52] U.S. Cl. ....................................... 604/87; 604/89; 604/416; 604/191; 206/219; 424/1.1
[58] Field of Search ....................... 424/1.1, 9; 604/87, 604/416; 206/219, 365; 222/80; 404/82, 83, 89, 191

[56] References Cited

U.S. PATENT DOCUMENTS

| | | |
|---|---|---|
| 3,756,390 | 9/1973 | Abbey et al. |
| 4,018,222 | 4/1977 | McAleer et al. ............... 604/113 |
| 4,518,386 | 5/1985 | Tartaglia .......................... 604/89 |
| 4,994,043 | 2/1991 | Ysebaert ........................ 604/191 |

FOREIGN PATENT DOCUMENTS

| | | |
|---|---|---|
| 0211592 | 2/1987 | European Pat. Off. |
| 0221566 | 5/1987 | European Pat. Off. |
| 8601120 | 2/1968 | World Int. Prop. O. |

*Primary Examiner*—Robert A. Hafer
*Assistant Examiner*—Kerry Owens
*Attorney, Agent, or Firm*—Oblon, Spivak, McClelland, Maier & Neustadt

[57] ABSTRACT

A twin-chamber syringe has a pyrogen-free sterile solvent in the chamber averted from the needle, and in the second chamber facing the needle a charge of activity-sensitive human protein, introduced and lyophilized in a single operation in the syringe, where it is stored, in a quantity necessary for therapeutically effective administration. The invention also relates to the filling of the syringe and the potential it offers for immediate use of activity-sensitive human proteins and for self-administration at home.

12 Claims, No Drawings

TWIN-CHAMBER SYRINGE FILLED WITH A CHARGE OF ACTIVITY-SENSITIVE HUMAN PROTEIN AS ACTIVE SUBSTANCE

BACKGROUND OF THE INVENTION

1. Field of the Invention:

The present invention relates to a twin-chamber syringe containing a solvent and an active substance, and more particularly to a syringe containing a pyrogen-free, sterile solvent and an activity-sensitive human protein.

2. Discussion of the Background:

For a long time, twin-chamber syringes have been used where a pyrogen-free, sterile solvent is present in one chamber, and a charge, obtained by lyophilizing in the syringe itself, which is dissolved by the pyrogen-free water when the syringe is operated, and then injected, in the second chamber facing the needle.

There is, however, a number of active substances based on human plasma proteins which are activity-sensitive. That means they cannot be kept in solution at higher concentration and over reasonable periods of time, f.i. some hours, because the substance then looses biological activity or can even be degraded and precipitate in part. This is especially true for factor VIII. Preparations of this kind can only be used in a relatively low concentration at present. The concentration in ampoules sized as to be still acceptable for solutions to be injected is too low for injection solutions with a sufficient therapeutic efficiency. Therefore, they are used as infusion solutions. Because these necessarily have to be highly-diluted solutions, the infusion, and therefore the application of the active substance takes a long time. In most cases, however, a rapid application is desired to obtain an effect as fast as possible. However, even for moderately high concentrations of such active substances, the time required for an infusion is often too long as to prevent degradation or deterioration of the substance.

Up to now, for use in direct lyophilization in the twin-chamber syringe the concentrations which could be obtained in solutions were to low as to obtain a sufficient quantity of the substances in the chamber by a single lyophilization step. For the same reasons which apply to the use of more concentrated solutions, repeated filling and lyophilization in the chamber, however, is not possible, as, due to the activity-sensitivity of such human proteins, the protein would be damaged when the chamber is refilled.

SUMMARY OF THE INVENTION

It was now possible to obtain significantly higher concentrations in solutions of such proteins, which, with regard to their stability with time and to their concentration, are sufficient to introduce the active substance without damage into the syringe chamber in a single charging of the syringe chamber and immediate lyophilization, with the result that a syringe prepared in this way can be stored for a longer time, and the protein is only dissolved by the pyrogen-free solvent in the other syringe chamber at the time it is used and injected immediately. Thus, the time in solution prior to the actual application is at most a couple of minutes.

Detailed Description of the Preferred Embodiments

In this way it is now possible to administer activity-sensitive human proteins in the high concentration desired, and therefore within a short period of time.

Such preparations are in particular urokinase, prourokinase, TPA, streptokinase, factor VIII and factor IX, and antithrombin III.

Thus, with the usual chamber sizes of such syringes of up to 6 ml for the chamber containing the solution (i.e. the active substance) to be lyophilized, and up to 4.5 ml for the solvent, at least 2 to 3 million units of urokinase, pro-urokinase, TPA, streptokinase, at least appr. 1000 units of factor VIII or factor IX, and at least appr. 500 to 1000 units of antithrombin III can be introduced into the syringe chamber for the active substance, by charging it with 3 to 3.5 $cm^3$ of the concentrated plasma.

A chamber with a volume of 6 ml cannot be charged with more than 3 to 3.5 $cm^3$ of the solution to be lyophilized, because during lyophilization the solution splashes and creeps up the wall. This emphasizes how important it is to use solutions with relatively high concentrations to charge the syringe, in order to accommodate therapeutically adequate amounts in the syringe chamber.

Such a syringe is now to be described in detail.

A twin-chamber syringe of a known type has the lyophilized active substance in the front, i.e. the second chamber lying next to the needle. The separate sealing cap, onto which the needle is mounted, is positioned on the left side of the neck of this chamber. Between the chambers there is a plate supplied with small holes which, when the plunger is pushed down, presses the solvent contained in the solvent chamber through the holes and the elevation formed by a projection of the syringe wall into the front chamber, where by short shaking the lyophilized active substance is dissolved, and the contents of the syringe can be administered immediately.

Because it is not possible to inject unlimited amounts of an injection solution, and the amount to be injected should not be too large, even in an injection i.v., the volume of chamber 1 can hardly exceed 6 ml. For this reason it is essential to accomodate as much of the acitve substance as possible by a single lyophilization step, i.e. at a time, in a chamber of up to this size.

Charging of the syringe is done in a known way by introducing under sterile conditions the given amount of a solution of the activity-sensitive human protein to be introduced, and then bringing the syringe to the next station where in situ lyophilization is carried out. The syringe with its lyophilized charge is then brought to the next station, where the pyrogen-free solvent is filled into the second chamber, followed by the final assembly and packing under sterile conditions. Automated machinery as customary for charging ready-to-use syringes can be used for this, with only slight alterations to allow for the syringe size, inserting the plunger, and the shape of the sealing cap of the syringe, which differs from the usual shape of such stoppers.

Such syringes are suited not only for use in f.i. surgery and hospitals, but also particularly in first-aid medicine, and for self-treatment by patients at home.

The process of concentrating solutions of the activity-sensitive human proteins will be illustrated in a number of examples. In this way, a significantly higher concentration can be obtained in solution than it was possible to obtain until now, so that a syringe chamber holding, f.i., 6 ml, which can be filled with not more than 3.5 ml for lyophilization, so that no spilling-over and creeping occurs during lyophilization, can be provided with one single lyophilization step with a sufficient amount of protein to provide in the charge of one single syringe the amount of protein sufficient for effective treatment.

The invention is further illustrated by the following examples.

EXAMPLE 1

Preparation of a concentrated solution of urokinase

Starting with appr. 1500 l urine, a bentonite-activator complex is prepared in a larger number of, f.i. appr, 50, batches, from which again crude urokinase is isolated in a known way. From the latter, a calcium phosphate-urokinase complex is formed in a number of batches, from which again concentrated urokinase with 500 000 to 600 000 I.U./ml, contained in a volume of 5-10 l, is isolated in two batches.

The details of the protocol are as follows:

Urine concentrated with boric acid is mixed with bentonite, the bentonite-activator complex is washed with water suitable for injection, eluted with a solution of 120 kg ammonium sulphate, 6.2 kg of a non-ionogenic ether glycol in the form of a bulk polymer, commercially available under the name of Pluronic, with water added to give 310 l, and the eluate is salted out with appr. 165 kg ammonium sulphate. The crude urokinase bulkware obtained is eluted with a solution of 0.9 kg ethacridinium lactate in 430 water suitable for injections, and the eluate is absorbed on a calcium phosphate gel, obtained from 11 kg sodium phosphate×12 $H_2O$, 6.4 kg calcium chloride×2 $H_2O$, with water added to give 180 l. The calcium-urokinase complex is eluted with a solution of appr. 12.5 kg sodium dihydrogen phosphate×2 $H_2O$, with 3 N sodium hydroxide solution added to give 220 l, and the eluate is purified on CM-cellulose, or CM-Sephadex, resp.. The CM-cellulose-urokinase complex thus obtained is eluted with a solution of 50 kg sodium dihydrogen phosphate×2 $H_2O$, with 3 N sodium hydroxide solution added to give 165 l, the eluate is acidified with phosphoric acid, pasteurized at 60° C. for appr. 10 h, dialyzed against 0.1 M phosphate buffer solution, and then filtered. The dialysate is then tested according to standard procedures for purified concentrated urokinase. Urokinase concentration usually ranges between 70 000 and 160 000 I.U./ml, and phosphate concentrations are the same as for 0.1 M phosphate buffer solution for dialysis. Optionally, the urokinase solution is diluted to the desired concentration by adding to the dialysate a suitable amount of albumin phosphate-buffer solution of pH 7.1 wherein the ratio of $NaH_2PO_4 \times 2 H_2O$ to $Na_2HPO_4 \times 12 H_2O$ is 13/60 by wt..

The solution with the desired concentration is then filled into syringes and lyophilized.

The following ion exchangers and membrane filters are used in the preparation procedure:

As ion exchanger carboxymethyl cellulose with an ion exchange capacity of 1.14 mEq/g dry weight, CM-Sephadex, type C-25, with an ion exchange capacity of $4.5 +/- 0.5$ mEq/g dry weight, and as membrane filter a polyamide filter with pore sizes of 0.2 μm, and 0.8 μm.

EXAMPLE 2

Preparation of a concentrated solution of antithrombin III

Isolation of antithrombin from blood plasma and blood products, in particular from the Cohn plasma fraction VI-1-paste, is done in a known way by purification by polyethylene glycol fractionation, affinity-chromatography on heparin-sepharose 4B, and heat treatment at 60° C. for 10 h. Doing this it is essential not to perform a gradient elution by means of a buffer with an increasing concentration of sodium chloride, but to maintain the concentration of the solvents for washing and elution, i.e. 0.4M NaCl, 0.02M imidazole solution, pH 7.2, for washing the column, and 2M NaCl, 0.02 imidazole solution, pH 6.5, for elution, constant all the time. The antithrombin III-solution obtained is concentrated through hollow fibres, mixed with sodium citrate, and stirred and pasteurized at 60° C. for 10 h. Then salts are removed by dialysis on hollow fibres. (Solvent for dialysis: $Na_3C_6H_5O_7 \times 2 H_2O$ (appr. 6 g), appr. 5 g NaCl, and 1N HCl or 1N NaOH to adjust the pH to 7.5, with water suitable for injection added to give 1000 ml.) The following steps were then performed under septic (non-sterile) conditions:

After adjusting the titer in the dialysate D-mannitose (20 g/l) is dissolved in it. pH is adjusted to 7.5 with 1N HCl or 1N NaOH followed by filtration through a membrane filter with a pore size of 0.45 μm, and the solution is filled into the syringe chamber for lyophilization. The activity of this solution is 300 to 350 I.U./ml.

EXAMPLE 3

Preparation of a concentrated solution of human anti-hemophilic factor (AHF or factor VIII, resp.)

AHF is prepared from pooled human plasma with the polyethylene glycol method. The frozen plasma is thawed under controlled temperature conditions, and the cryo-precipitate is recovered by centrifugation, resuspended in heparinized distilled water (80 U heparin per ml), and the pH of the solution is adjusted to 7.0 with diluted HCl, and then it is resuspended at 28° C. by gentle mixing. The volume of the heparinized water is appr. 3 l/kg cryo-precipitate.

Polyethylene glycol is then added to the AHF solution in a final concentration of 3%, and admixed well at 25° C. The pH of the AHF solution is then adjusted to 6.3 with diluted acetic acid. The suspension is then mixed at 25° C. for at least appr. ¼ h, followed by centrifugation.

The supernatant after centrifugation is filtered to remove all solid particles. Then tri-n-butyl phosphate and Polysorbat 80 are added to the filtered AHF solution to a final concentration of 0.30% TNBP (vol./wt.) and 1% Polysorbat (wt./wt.). The pH is adjusted to 6.3 with diluted acetic acid, and the mixture is left to stand at 27° C. over night. Then more PEG is added to a final concentration of 12%. The suspension is mixed for some time at 25° C., as described above, and the AHF precipitate formed is recovered by centrifugation.

The PEG-precipitated AHF is resuspended at 5° C. in 1.6M glycine solution, containing 0.23M citrate and 13 U/l heparin. The volume of the glycine solution is 20 l/kg precipitated AHF. When the suspension is mixed to homogeneity, the AHF precipitate is recovered by centrifugation.

The glycine-precipitated AHF is resuspended again in glycine solution, again containing citrate and heparin, at 5° C. The volume of the glycine solution is 20 l/kg precipitated AHF. After mixing of the solution to homogeneity the AHF precipitate is again recovered by centrifugation.

This precipitate is resuspended in 0.4M EDTA (pH 7.3–7.5) (8 l/kg), and dialyzed against washing buffer (0.02M sodium citrate, 0.05M sodium chloride, pH 6.6 to 7.0).

This can be repeated several times until the desired concentration is reached.

As an alternative, this precipitate can be dissolved in glycine-sodium citrate solution at 20° C., where the pH is adjusted with diluted NaOH or HCl to 7.3. The volume of the glycine-sodium citrate solution is 20 l/kg glycine-precipitated AHF. This solution is then sterilized by filtration through previously sterilized membrane filters holding back bacteria, filled into the syringes under aseptic conditions, and lyophilized. The concentration is appr. 300 to 350 I.U./ml.

EXAMPLE 4

Preparation of factor IX

The factor IX complex-powder (prothrombin complex) obtained in the usual way is dissolved in distilled water at a protein concentration of 1.2%. It is then mixed with diluting buffer (0.02M sodium citrate, 0.25M sodium chloride, pH 7.3; 4.0 l/l), and 0.16 l 1M barium chloride solution per liter is added to precipitate factor IX protein. The precipitated protein is recovered by filtration or centrifugation, then dissolved in a solution of 0.4M EDTA at 8 l/kg, and diafiltered with washing buffer (0.02M sodium citrate, 0.05M sodium chloride). The diafiltered factor IX is repeatedly applied to a chromatography column containing dextrane sulphate-SiO$_2$-resin, and eluted, until the desired concentration is reached. The amount of resin in the column is appr. 2.5 l/100 g processed starting material.

The factor IX absorbed on the resin is washed in the column with 10 or more volumes of washing buffer, which is then discarded. Purified factor IX is eluted from the resin with a linear salt gradient by gradually increasing the amount of an elution buffer consisting of 0.02M sodium citrate and 0.5M sodium chloride, pH 6.6 to 7. At the end of the gradient the column is further eluted with additional elution buffer. The factor IX eluate is pooled, filtered, and, optionally after diafiltration, pH adjusted to 7, filled into the syringes and lyophilized. The average concentration of the solution is appr. 300 to 350 I.U./ml.

I claim:

1. A method for producing a twin-chamber syringe having a first chamber and a second chamber, said first and second chambers being separated by a rupturable barrier, said second chamber being in fluid communication with an injection needle, said first chamber containing a pyrogen-free solvent and said second chamber containing activity-sensitive human protein, comprising the steps of:
    (a) charging said second chamber with a solution of said activity-sensitive human protein of sufficient concentration to provide a single therapeutically effective dose of said protein,
    (b) lyophilizing said solution directly in said second chamber to obtain lyophilized protein in said second chamber,
    (c) filling said first chamber with pyrogen-free solvent to prepare a filled syringe, and
    (d) sterilizing said filled syringe.

2. The method of claim 1, wherein said lyophilized protein consists of at least 2–3 million units of urokinase.

3. The method of claim 1, wherein said lyophilized protein consists of at least 2–3 million units of prourokinase.

4. The method of claim 1, wherein said lyophilized protein consists of at least 2–3 million units of tissue plasminogen activator.

5. The method of claim 1, wherein said lyophilized protein consists of at least 2–3 million units of streptokinase.

6. The method of claim 1, wherein said lyophilized protein consists of at least about 1000 units of factor VIII.

7. The method of claim 1, wherein said lyophilized protein consists of at least about 1000 units of factor IX.

8. The method of claim 1, wherein said lyophilized protein consists of at least about 500–1000 units of antithrombin III.

9. The method of claim 1, wherein said concentrated solution of activity-sensitive human protein is obtained by dialyzing and chromatographing said activity-sensitive human protein.

10. The method of claim 9, wherein said activity-sensitive human protein is purified by mixing with polyethylene glycol followed by centrifuging prior to said dialyzing and chromatographing steps.

11. The method of claim 9, wherein said dialyzing step is performed from a basic solution against an acidic buffer, and in said chromatographing step, elution is performed with an acidic buffer.

12. The method of claim 11, wherein during said dialyzing step, said basic solution has a pH of 7.3–7.5 and said acidic buffer has a pH of 6.6–7.0, and during said chromatographing step, said acidic buffer has a pH of 6.6–7.0.

* * * * *